United States Patent
Bentien

(10) Patent No.: US 9,528,944 B2
(45) Date of Patent: Dec. 27, 2016

(54) MONITORING SYSTEM

(75) Inventor: Anders Bentien, Skødstrup (DK)

(73) Assignee: Grundfos Management a/s, Bjerringbro (DK)

( * ) Notice: Subject to any disclaimer, the term of this patent is extended or adjusted under 35 U.S.C. 154(b) by 0 days.

(21) Appl. No.: 13/996,197

(22) PCT Filed: Nov. 25, 2011

(86) PCT No.: PCT/EP2011/071060
§ 371 (c)(1),
(2), (4) Date: Jun. 20, 2013

(87) PCT Pub. No.: WO2012/084409
PCT Pub. Date: Jun. 28, 2012

(65) Prior Publication Data
US 2013/0293873 A1    Nov. 7, 2013

(30) Foreign Application Priority Data
Dec. 21, 2010    (EP) .................................. 10015858

(51) Int. Cl.
G01N 21/94    (2006.01)
G01N 15/02    (2006.01)
G01N 15/00    (2006.01)
G01N 15/14    (2006.01)

(52) U.S. Cl.
CPC .......... *G01N 21/94* (2013.01); *G01N 15/0227* (2013.01); *G01N 2015/0088* (2013.01); *G01N 2015/1486* (2013.01)

(58) Field of Classification Search
CPC ................................ G01N 21/00; G01N 21/94
USPC ........................................................... 256/73
See application file for complete search history.

(56) References Cited

U.S. PATENT DOCUMENTS 3,102,200 A * 8/1963 Rich ............................. 250/389
3,738,751 A * 6/1973 Rich .............................. 356/37
5,880,835 A * 3/1999 Yamazaki ............ G01N 15/147
356/336

(Continued)

OTHER PUBLICATIONS

Int'l Search Report and Written Opinion issued Jan. 31, 2012 in Int'l Application No. PCT/EP2011/071060.

(Continued)

*Primary Examiner* — Tarifur Chowdhury
*Assistant Examiner* — Omar Nixon
(74) *Attorney, Agent, or Firm* — Panitch Schwarze Belisario & Nadel LLP

(57) ABSTRACT

A monitoring system (2) for monitoring the number and/or concentration of particles and/or micro organisms (12, 22) in a fluid (10). The monitoring system (2) generates an alarm if a predefined criterion is met. The monitoring system (2) includes a micro processor (6) which executes programmed instructions in order to identify and classify particles (12), a storage member (8), and an optical sensor member (40) having a 2-D optical sensor (4) and a light source (36). The optical sensor member (40) records an image of a part of the fluid (10) and the monitoring system (2) determines the number and/or concentration of particles (12) in the fluid (10) on the basis of the optical response of single particles (12) in a sample zone (38) in the fluid (10). The fluid (10) in the sample zone (38) is kept stationary relative to the optical sensor member (40) during the image recording.

13 Claims, 3 Drawing Sheets

(56) References Cited

U.S. PATENT DOCUMENTS

| | | | |
|---|---|---|---|
| 6,040,191 A | 3/2000 | Grow | |
| 2003/0030810 A1* | 2/2003 | Sebok | G01N 15/147 356/436 |
| 2004/0165185 A1* | 8/2004 | Reintjes et al. | 356/335 |
| 2006/0232780 A1* | 10/2006 | King | G01N 15/1404 356/436 |
| 2006/0274309 A1* | 12/2006 | Cerni et al. | 356/338 |
| 2007/0194244 A1 | 8/2007 | Adams et al. | |
| 2007/0272877 A1* | 11/2007 | Tribelsky et al. | 250/431 |
| 2008/0076147 A1* | 3/2008 | El-Azizi et al. | 435/30 |
| 2008/0221711 A1 | 9/2008 | Trainer | |
| 2009/0219530 A1* | 9/2009 | Mitchell | G01N 15/1459 356/336 |
| 2011/0066382 A1* | 3/2011 | Adams | 702/19 |

OTHER PUBLICATIONS

Office Action issued Jun. 12, 2014 in EP Application No. 10015858.3.

\* cited by examiner

MONITORING SYSTEM

CROSS-REFERENCE TO RELATED APPLICATIONS

This application is a Section 371 of International Application No. PCT/EP2011/071060, filed Nov. 25, 2011, which was published in the English language on Jun. 28, 2012, under International Publication No. WO 2012/084409 A1 and the disclosure of which is incorporated herein by reference.

BACKGROUND OF THE INVENTION

Online, robust, reagentless and low maintenance sensors that detect the presence and concentration of bacteria in fluids will have potential use in many areas where a continuous monitoring of bacteria can ensure microbial quality or decrease the number of manually collected samples and measurements. An example is related to monitoring microbial water quality in wells/water intake, water works and/or water distribution system.

Methods for analysis of particles in liquid samples are known from the prior art. In some of these methods, a plurality of images of the fluid is recorded and further analyzed in order to identify the characteristics of the particles.

Currently, the most advanced box-product online sensors and alarm systems for monitoring (microbial) water quality are turbidity sensors and particle counters. Turbidity, however, is only an indicative measurement, as it is not only bacteria that can change the turbidity of water. Furthermore, turbidity sensors lack sensitivity and have a relatively poor detection limit. On-line box-product particle counters for water quality measurements do have the sensitivity and detection limit required. They can, however, only detect particles with diameters down to 1-2 µm. Bacteria in water have sizes from 0.3 µm to 3 µm, with most of them having sizes below 1 µm. Thus, current particle counters are not effective for detecting bacteria in liquids and they cannot discriminate between bacteria and other particles. Furthermore, particle counters are prone to errors in the readout if there are deviations in the relatively large and constant flow (>50 ml/minute) through the measurement unit. The constant flow is often ensured by a large tubing system that utilizes gravity to ensure the constant flow.

Thus, the constant flow requirement is one of the main disadvantages of the prior art systems. Moreover, the online methods available on the market require huge amounts of water during the measurement period. In many applications (e.g., in a well), there are no drains available and thus the known systems cannot be used.

BRIEF SUMMARY OF THE INVENTION

It is an object of the present invention to provide a particle and/or micro organisms monitoring and alarm system that does not require a constant flow and access to a drain.

This object can be achieved by a monitoring system having the features defined in claim 1. Additional embodiments are disclosed in the sub claims, the following description and the drawings.

The monitoring system for monitoring the number and/or concentration of particles in a fluid according to embodiments of the present invention includes:
- a micro processor configured to execute programmed instructions in order to identify and classify particles;
- a storage member; and
- an optical sensor member including:
  - a 2-D optical sensor and
  - a light source.

The optical sensor member is configured to record at least one image of at least a part of the fluid. The monitoring system (2) is configured to generate an alarm if a predefined criterion is met.

The monitoring system is configured to determine the number and/or concentration of particles in the fluid on the basis of the optical response of single particles in a sample zone in the fluid. Preferably, the fluid in the sample zone is kept stationary relative to the optical sensor member during the recording of an image.

Particles are considered to be all objects of interest in the fluid. Particles may be micro organisms, such as alga, parasites or bacteria by way of example. These micro organisms may be in the diameter range of 0.3-20 µm. However, this range is not a limit. In fact, the monitoring system according to embodiments of the present invention is, in principle, capable of detecting all types of particles present in the fluid. Preferably, the current sensor is capable of detecting particles and microorganisms down to 0.3 µm and the upper limit is restricted by the dimensions of tubing a flow cell and is of the order 1 mm. Thus, the current sensor covers the size range of microorganisms in water.

The predefined criterion may be any suitable criterion. However; it may be preferred that the criterion is related to the particle content in the fluid. By way of example, the predefined criterion may be the concentration of bacteria.

The monitoring system may include one or more image sensors, lens systems and light sources.

Preferably, the sampling zone is filled up with the fluid prior to each recording. Hereby, it is achieved that the sample zone is kept stationary relative to the sensor member during the recording of each image. Thus, the need for flow regulation (to provide a constant flow) is eliminated.

Keeping the fluid in the sample zone stationary relative to the optical sensor member during the recording of an image eliminates the need for a constant flow. Moreover, during operation, the fluid that is being measured can be kept at the system pressure (this may be over 10 bar) of the well, inlet, water work and/or distribution network and after measurement the liquid (<1 ml/minute) is preferably not necessarily wasted into a drain, and can therefore easily be recycled into the system, thereby eliminating the need for a drain.

In one embodiment of the present invention, the monitoring system has an optical sensor member that includes at least one lens system. A lens system may include one or more lenses that may diffuse or focus the light. On the other hand, it may be possible to have a monitoring system that does not have a lens system.

In one embodiment of the present invention, the monitoring system is configured to determine the number of micro organisms in the fluid on the basis of the optical response of micro organisms.

Thus, this embodiment makes it possible to provide online measurements of the micro organism (e.g. bacteria) level. This information can be provided without having advanced and expensive devices to provide a constant flow. In many applications, such as in water distribution systems, online measurements are extremely valuable.

In one embodiment of the present invention, the micro processer is adapted to determine the number and/or concentration of particles and/or micro organisms and generate an alarm if:

a) the number and/or concentration of particles and/or micro organisms exceeds a first preset value, and/or
b) the rate of increase in the number and/or concentration of particles and/or micro organisms exceeds a second preset value, and/or
c) the change in morphology of the particles and/or micro organisms meets a first preset criterion, and/or
d) the change in size of the particles and/or micro organisms meets a second preset criterion.

The morphology of a particle and/or a micro organism may be defined in terms of the eccentricity defined as the ratio between the longest and the shortest diameter of the particle and/or micro organism.

The size of a particle and/or a micro organism may be defined as the largest diameter of the particle and/or a micro organism.

By the term alarm is meant any suitable type of alarm. The alarm may, by way of example, be a visual signal, a sound, and/or a message sent to a computer, mobile phone or any other type of receiving unit.

Hereby, it is preferably achieved that an alarm can be generated when at least one preset criterion is met. It would, in particular, be possible to generate the alarm when undesirable conditions occur. This may be beneficial in relation to water distribution by way of example.

In another embodiment of the present invention, the monitoring system comprises a 2-D optical sensor that is configured to record a number of images of the fluid and the monitoring system, and is configured in a way such that the relative position of the focal plane of the optical sensor member with respect to the fluid is varied.

Hereby, it is achieved that several parameters can be detected from the images. Accordingly, the monitoring system may be used to differentiate the characteristics of the particles and/or micro organisms.

In one embodiment of the present invention, the monitoring system comprises a 2-D optical sensor, a micro processer, a storage member and a lens system that are built together in one sensor unit.

In some applications, is would be beneficial to use a sensor unit that includes an optical sensor member, a micro processer, a storage member and a lens system. This sensor unit may be a one-piece member provided in a housing. This way of installing the monitoring system is easy and subject to less risk of installation failures.

It is also possible to use a sensor unit that includes an optical sensor member, a micro processer, and a storage member. In this embodiment, there is no lens system since the lens system may be omitted. The lens system is not needed if the optical sensor member includes a special light source that emits light that does not need to be diffused or focused.

In another embodiment of the present invention, the monitoring system includes at least a first optical sensor member and a second optical sensor member. The monitoring system may be configured to determine:
a) the number and/or concentration of particles and/or micro organisms per unit time, and/or
b) the rate of increase in the number of particles and/or micro organisms per unit, and/or
c) the morphology of the particles and/or micro organisms per unit time, and/or
d) the size of the particles and/or micro organisms.

Preferably, the determinations are based on the images recorded by the first optical sensor member and the second optical sensor member, respectively.

In one embodiment of the present invention, the monitoring system includes at least a first optical sensor member and a second optical sensor member that are arranged in a way, such that at least the first optical sensor members and the second optical sensor members use the same light source.

In another embodiment of the present invention, the monitoring system is configured to calculate the difference between parameters determined on the basis of measurements based on images recorded by at least the first optical sensor member and the second optical sensor member, respectively.

The use of more than one optical sensor member may provide additional image information that can be used to provide a more detailed determination of the particle and/or micro organism content of the fluid. The optical sensor members may be arranged in any suitable way so that as much additional information as possible can be achieved from the recorded images. Moreover, the use of more than one optical sensor member enables calculation of differences and in the particle and/or micro organism content of the fluid.

Hereby it is achieved that differences between different areas can be detected. The optical 2-D sensors may be arranged in different areas in a network and the distance between the optical sensor members may be chosen in order to meet specific demands or requirements. It would be possible to gather information about the different areas and to compare this information.

In one embodiment of the present invention, the monitoring system includes at least two sensor units that are configured to communicate with a central control device. Hereby, it is possible to carry out a direct comparison of information provided by using several sensor units. Each sensor unit may include specific information that can be used to indicate the particle and/or micro organism level. Information from several sensor units may be used to provide information of even more value, since the difference calculated on the basis of the information from the different sensor units may be used to determine and evaluate changes in the particle or micro organism content and the gradient of these changes. It would be possible to use a control device that is contained in one of the at least two sensor units.

In another embodiment of the present invention, the monitoring system is configured to generate an alarm if at least one preset criterion based on information from at least two sensor members is met. Hereby, it is achieved that the monitoring system is adapted to give a warning in case of the occurrence of an increase in the micro organism and/or particle content, by way of example. The nature of a criterion can be limited to specific types of micro organisms and/or particles. However, it would also be possible to use a criterion that not is limited to any specific types of micro organisms and/or particles. In fact, difference between any set of parameters may be compared to preset values in order to generate an alarm.

In another embodiment of the present invention, the monitoring system includes an inlet valve and an outlet valve that are configured to be closed so that the fluid inlet and outlet is eliminated during the optical exposure of the 2-D optical sensor. In this way, the monitoring system is capable of keeping a constant volume of the fluid in a space so that one or more images may be recorded without having to use the complicated means for providing a constant flow.

It would be possible to use a monitoring system having valves that are being controlled by a control system that also is capable of controlling a pump that is configured to replace the fluid in the flow cell so that new images can be recorded.

In one embodiment of the present invention, the optical sensor member is configured to be displaced along the longitudinal axis or another axis of the optical area sensor. By displacing the sensor member along the longitudinal axis of the optical area sensor, it is possible to gather information about the content of micro organisms and/or particles in the total fluid volume of the flow cell. Thus, the required information can be collected in a simple and easy manner.

In one embodiment of the present invention, the optical sensor member is configured to be displaced along the longitudinal axis or another axis of a flow cell.

The optimal direction of displacement may depend on the construction of the monitoring system. Accordingly, in some applications it may be beneficial to displace the optical sensor member in one direction, while it may be an advantage to displace the optical sensor member in another direction in other applications.

In one embodiment of the present invention, the monitoring system includes several sensors units disposed in a network. Accordingly, it would be possible to provide a rather precise location of a source of pollution by way of example. In a water distribution network, it would be possible to apply three or more sensor units so that the source of pollution can be detected with a rather high precision in case of pollution. The network may in principle be of any size scale. Thus, a network may be a local pipe network in a factory or a huge water distribution network in a town, by way of example.

One embodiment of the present invention relates to a method for analysis of particles in a liquid sample by a measurement system, as described in one or more of the claims.

The monitoring system may include members or mechanisms for detecting flow direction, volume of a container and the time the fluid is kept in a container. Moreover, temperature and acidity may be detected. These parameters may be used to draw an even more precise picture of the status of the fluid and/or system that is being monitored by the monitoring system.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

The present invention will become more fully understood from the detailed description given herein below and the accompanying drawings are given by way of illustration only, and thus, they are not limitative of the present invention, and wherein:

In the drawings:

FIG. 1 shows a monitoring system according to embodiments of the present invention;

FIG. 2 shows the level of detected particles or bacteria in a fluid versus time according to embodiments of the present invention; and FIG. 3 shows a schematic view of the monitoring system applied in a network according to embodiments of the present invention.

DETAILED DESCRIPTION OF THE INVENTION

Other objects and further scope of applicability of embodiments of the present invention will become apparent from the detailed description given hereinafter. It should me understood, however, that the detailed description and specific examples, indicating preferred embodiments of the invention, are given by way of illustration only, since various changes and modifications within the spirit and scope of the invention will be become apparent to those skilled in the art from this detailed description.

Figure 1:
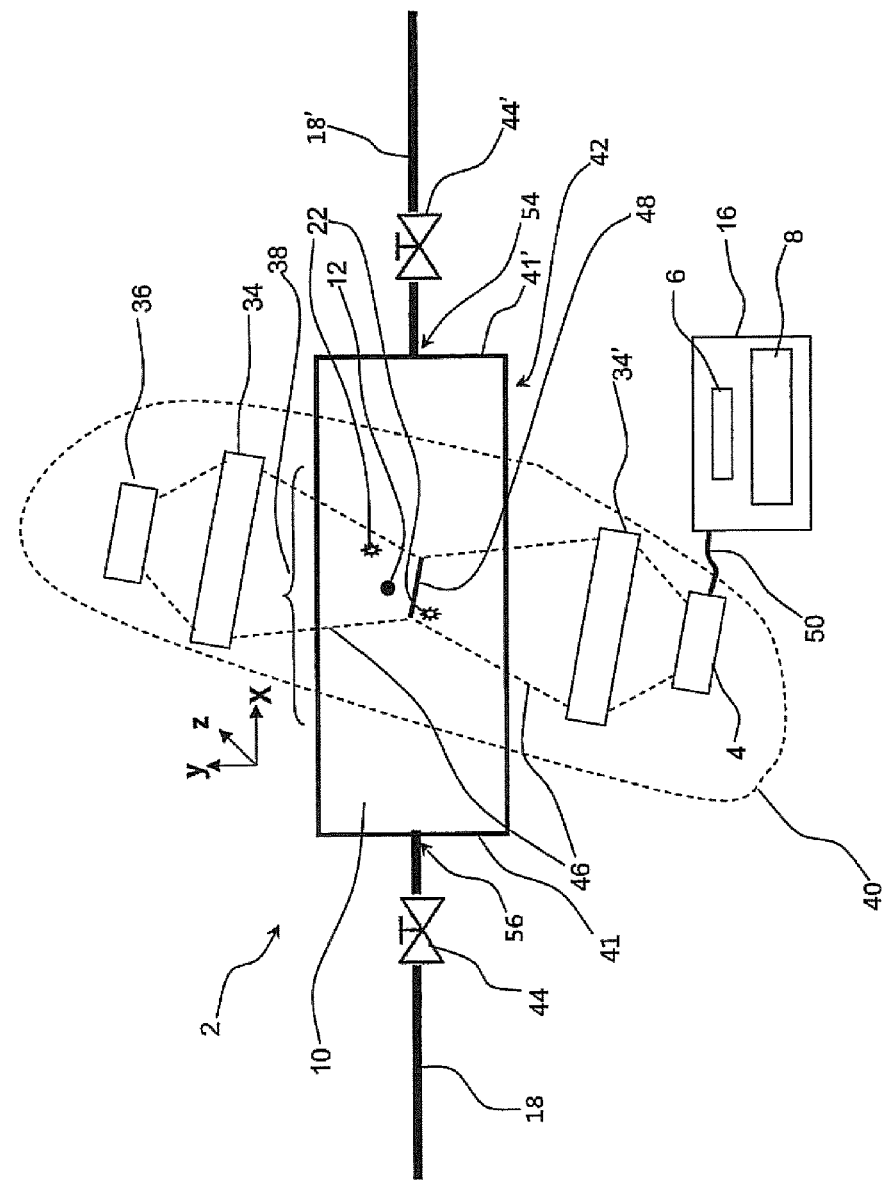

Referring now in detail to the drawings for the purpose of illustrating preferred embodiments of the present invention, elements of a monitoring system 2 according to embodiments of the present invention are illustrated in FIG. 1. The monitoring system 2 includes a flow cell 42 having an inlet 54 and an outlet 56 through which a fluid 10 can be channelled. The fluid 10 may be pumped through the flow cell 42 by using a suitable pump (not shown) that may be arranged either at the inlet pipe 18' or the outlet pipe 18, by way of example.

Adjacent to the end sides 41, 41' of the flow cell 42, an outlet valve 44 is provided at the outlet pipe 18 that is connected to the flow cell 42. At the other end of the flow cell 42, an inlet valve 44' is provided at the inlet pipe 18' that is configured to channel fluid 10 to the flow cell 42. The fluid 10 contains particles 12 and/or micro organisms 22.

The monitoring system 2 is moreover provided with an optical sensor member 40 that comprises a 2-D optical sensor 4, two lens systems 34, 34' and a light source 36. The light source 36 may be a light-emitting diode (LED) by way of example. Other suitable types of light sources may be used. Light 46 from the light source 36 enters the first lens system 34 and is directed toward the focal plane 48 where the particles 12 and/or micro organisms 22 of interest are present. The first lens system 34 attenuates the light signal 46 that enters the second lens system 34' that depicts the attenuated light signal in the focal plane 48 into a recording 2-D optical sensor 4.

It is of importance to embodiments of the present invention that the liquid 10 in the flow cell 42 is kept still relative to the optical sensor member 40, because the monitoring system 2 does not have a mechanism for providing a constant flow. The term "kept still" should be interpreted so that the average speed of the fluid 10 is close to zero. This may optionally be obtained by closing the outlet valve 44 and/or the inlet valve 44'. Between each recording, the optical sensor member 40 may optionally be moved in the x direction and/or y direction and/or z direction relative to the flow cell 42. It is also possible to displace the optical sensor member 40 in a direction that is a linear combination of two or more of the indicated x, y or z directions. This motion may be achieved by using a step motor (not shown) by way of example. Other suitable mechanisms or methods may be used to perform the required translation of the optical sensor member 40. In fact, it would possible to displace the optical sensor member 40 in any desired direction along any suitable axis. By way of example, it is possible to displace the optical sensor member 40 along the longitudinal axis x of the flow cell 42.

The monitoring system 2 is capable of eliminating the use of a mechanism for providing a constant flow in the sampling zone 38. Since the providing of a constant flow in the sampling zone 38 requires advanced and expensive devices, embodiments of the present invention offer a simple and reliable solution to this problem. In addition, the monitoring system 2 recycles the fluid 10 that is being monitored, and thus, the monitoring system 2 can be used in applications (e.g., in a well) in which there are no drains available.

A control device 16 including a micro processor 6 and a storage member 8 is connected to the 2-D optical sensor 4 through a wire 50. Alternatively, it is possible to transfer data from the 2-D optical sensor 4 to the control device 16 wirelessly. This can be achieved by providing the 2-D optical sensor 4 with a transmitter (not shown) capable of sending information wirelessly to a receiver connected to or contained in the control device 16. The data recorded by the 2-D optical sensor 4 can be stored in the storage member 8 and the micro processor 6 can execute programmed instructions in order to identify and classify the particles 12 and/or micro organisms 22.

When referring to particles, all objects of interest in the fluid 10 should be included. The particles may, in particular, be micro organisms such as alga, parasites or bacteria, by way of example. These micro organisms of interest may be in the range of 0.3-20 micrometers.

Figure 2:
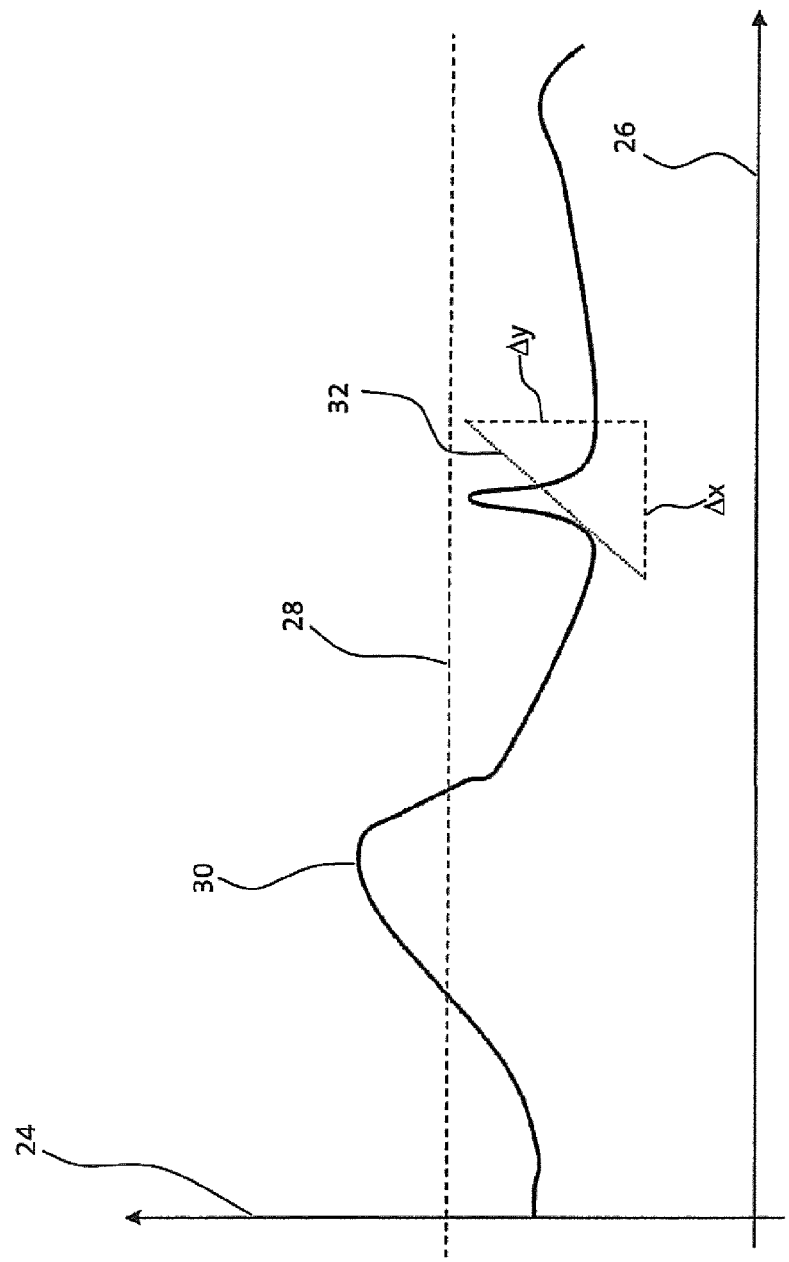

FIG. 2 illustrates the number 24 of detected bacteria in a fluid versus time 26. The curve 30 is a function of time 26 and it can be seen that the number of detected bacteria exceeds a preset value 28. When this preset value 28 is exceeded, the monitoring system may generate an alarm so that the user of the monitoring system is aware that the preset value 28 is exceeded. In some situations, the rate of increase in the concentration of particles and/or bacteria per unit time is of more interest than the number of bacteria or bacteria concentration itself. The curve 30 actually shows that the rate of increase in the concentration of bacteria exceeds a second preset value 32, since the slope of the curve 30 exceeds the preset maximal rate of increase 32. Therefore, the monitoring system may generate an alarm to make the user of the monitoring system aware of the high rate of increase in the concentration of bacteria.

The illustration in FIG. 2 shows the bacteria content in a fluid. However, the same principles may be used in relation to other particles and/or micro organisms. Thus, in principle, a curve 30, like the one shown in FIG. 2, could be used to evaluate whether the actual level or the rate of increase in the number and/or concentration of any detectable type of particles and/or micro organisms is above a critical level, so that an alarm should be generated.

Figure 3:
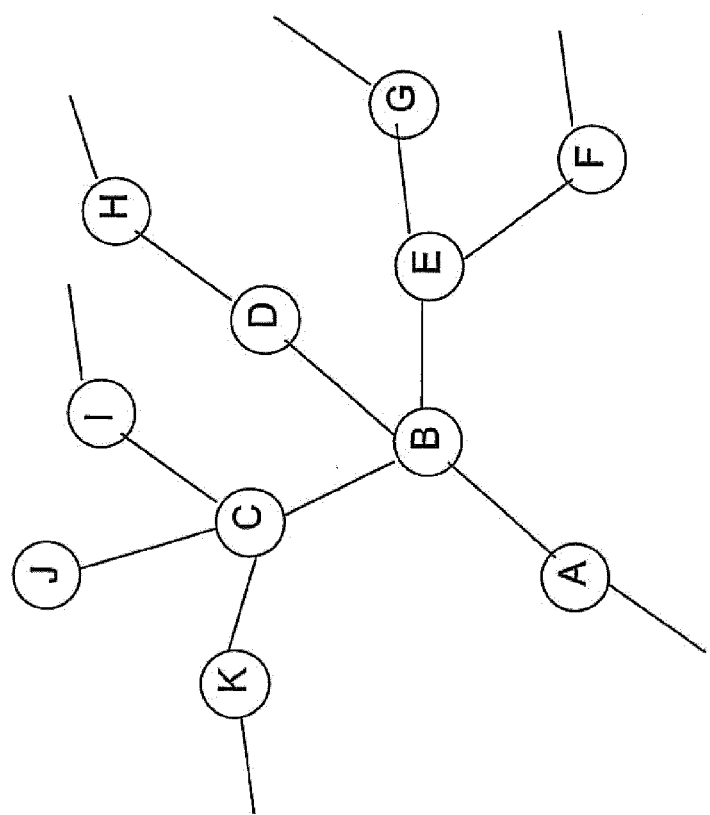

FIG. 3 illustrates a monitoring system that includes eleven sensor units A, B, C, D, E, F, G, H, I that are arranged within a network 58. Preferably, the monitoring system is connected to one or more (central) control units that receive information from the sensor units A, B, C, D, E, F, G, H, I. Each sensor unit A, B, C, D, E, F, G, H, I determines the number and/or concentration of particles and/or micro organisms in the fluid that is being monitored. Therefore, each sensor unit A, B, C, D, E, F, G, H, I collects information of a specific area in the network 58.

On the basis of the information from each of these sensor units A, B, C, D, E, F, G, H, I, it is possible to monitor and detect the location of increase in the number and/or concentration of particles and/or micro organisms. Accordingly, the monitoring system is capable of identifying the existence and exact location of a source of pollution. In water distribution networks, one of the real-life challenges is to locate the source of pollution. Therefore, it would be very valuable to have a monitoring system that is capable of identifying the existence and exact location of a source of pollution. This would result in both time and cost savings.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A monitoring system (2) for monitoring the number and/or concentration of particles (12, 22) in a fluid (10), the monitoring system (2) comprising:
   a micro processor (6) configured to execute programmed instructions in order to identify and classify particles (12);
   a storage member (8);
   an optical sensor member (40) comprising a 2-D optical sensor (4) and a light source (36), the optical sensor member (40) being configured to record a plurality of images of at least a part of the fluid (10) during a recording by varying the relative position of a focal plane of the optical sensor member (40) with respect to the fluid, and the monitoring system (2) being configured to generate an alarm if a predefined criterion is met;
   a flow cell (42) having an inlet valve (44'), an outlet valve (44), and a sample zone (38), the inlet and outlet valves (44', 44) being configured to be closed so that a fluid inlet (54) and a fluid outlet (56) of the flow cell are closed during optical exposure of the 2-D optical sensor (4); and
   a control system configured to control (i) the inlet and outlet valves (44', 44) to replace the fluid (10) in the flow cell (42), and (ii) a pump that is configured to replace the fluid (10) in the flow cell (42) so that new images can be recorded,
   wherein the monitoring system (2) is configured to determine the number and/or concentration of particles (12) in the fluid (10) on the basis of the optical response of single particles (12) in the sample zone (38) in the fluid (10),
   wherein the fluid (10) in the sample zone (38) is kept stationary relative to the optical sensor member (40) during each recording of a plurality of images,
   wherein the monitoring system (2) maintains a constant volume of the fluid in the sample zone (38), and
   wherein, between each recording of a plurality of images, the optical sensor member (40) is moved in an x and/or y and/or z direction.

2. The monitoring system (2) according to claim 1, wherein the optical sensor member (40) comprises at least one lens system (34).

3. The monitoring system (2) according to claim 1, wherein the monitoring system (2) is configured to determine the number of micro organisms in the fluid (10) on the basis of the optical response of the micro organisms.

4. The monitoring system (2) according to claim 1, wherein the micro processes (6) is configured to determine the number and/or concentration of particles (12) and/or micro organisms and generate an alarm if:
   a) the number and/or concentration of particles (12) and/or micro organisms exceeds a first preset value (28),
   b) the rate of increase in the number and/or concentration of particles (12) and/or micro organisms exceeds a second preset value (32), c) the change in morphology of the particles (12) and/or micro organisms meets a first preset criterion, and/or d) the change in size of the particles (12) and/or micro organisms meets a second preset criterion.

5. The monitoring system (2) according to claim 4, wherein the monitoring system (2) comprises at least a first optical sensor member (40) and a second optical sensor.

6. The monitoring system (2) according to claim 5, wherein the monitoring system (2) is configured to calculate the difference between parameters determined on the basis of measurements based on images recorded by the at least the first optical sensor member (40) and the second optical sensor member, respectively.

7. The monitoring system (2) according to claim 6, wherein the monitoring system (2) comprises at least two sensor units and the at least two sensor units are configured to communicate with a central control device (16).

8. The monitoring system (2) according to claim 7, wherein the monitoring system (2) is configured to generate an alarm if at least one preset criterion based on information from the at least two sensor members is met.

9. The monitoring system (2) according to claim 2, wherein the optical sensor member (40), the micro processer (6), the storage member (8) and the lens system (34, 36) are built together in one sensor unit (16).

10. The monitoring system (2) according to claim 1, wherein the optical sensor member (40) is configured to be displaced along a longitudinal axis (X) of a flow cell (42).

11. A method for analysis using a monitoring system according to claim 1, the method comprising analyzing particles in a liquid sample.

12. A monitoring system (2) for monitoring the number and/or concentration of particles (12, 22) in a fluid (10), the monitoring system (2) comprising:
 a micro processer (6) configured to execute programmed instructions in order to identify and classify particles (12);
 a storage member (8);
 an optical sensor member (40) comprising a 2-D optical sensor (4) and a light source (36), the optical sensor member (40) being configured to record a plurality of images of at least a part of the fluid (10) during a recording by varying the relative position of a focal plane of the optical sensor member (40) with respect to the fluid, and the monitoring system (2) being configured to generate an alarm if a predefined criterion is met; and
 a flow cell (42) having an axis,
  wherein the monitoring system (2) is configured to determine the number and/or concentration of particles (12) in the fluid (10) on the basis of the optical response of single particles (12) in a sample zone (38) in the fluid (10),
  wherein the fluid (10) in the sample zone (38) is kept stationary relative to the optical sensor member (40) during each recording of a plurality of images, and
  wherein, between each recording of a plurality of images, the optical sensor member (40) is moved in an x and/or y and/or z direction.

13. A monitoring system (2) for monitoring the concentration of particles (12, 22) in a fluid (10), the monitoring system (2) comprising:
 a micro processer (6) configured to execute programmed instructions in order to identify and classify particles (12);
 a storage member (8);
 an optical sensor member (40) comprising a 2-D optical sensor (4) and a light source (36), the optical sensor member (40) being configured to record at least one image of at least a part of the fluid (10); and
 a flow cell (42) having an inlet valve (44'), an outlet valve (44), and a sample zone (38), the inlet and outlet valves (44', 44) being configured to be closed so that a fluid inlet (54) and a fluid outlet (56) of the flow cell are closed during optical exposure of the 2-D optical sensor (4),
  wherein the monitoring system (2) is configured to determine the concentration of particles (12) in the fluid (10) on the basis of the optical response of single particles (12) in the sample zone (38) in the fluid (10),
  wherein the fluid (10) in the sample zone (38) is kept stationary relative to the optical sensor member (40) during the recording of the at least one image, and
  wherein the monitoring system (2) maintains a constant volume of the fluid in the sample zone (38).

* * * * *